(12) United States Patent
Cho et al.

(10) Patent No.: US 8,377,049 B2
(45) Date of Patent: Feb. 19, 2013

(54) SURGICAL INSTRUMENT

(75) Inventors: Seong-Yeon Cho, Goyang-si (KR);
Sang-Jae Park, Goyang-si (KR);
Kwang-Gi Kim, Goyang-si (KR)

(73) Assignee: National Cancer Center, Gyeonggi-Do (KR)

( * ) Notice: Subject to any disclaimer, the term of this patent is extended or adjusted under 35 U.S.C. 154(b) by 791 days.

(21) Appl. No.: 12/583,734

(22) Filed: Aug. 24, 2009

(65) Prior Publication Data

US 2010/0286675 A1 Nov. 11, 2010

(30) Foreign Application Priority Data

May 6, 2009 (KR) .................. 10-2009-0039091

(51) Int. Cl.
*A61B 18/18* (2006.01)
(52) U.S. Cl. .................. 606/15; 606/207; 606/208
(58) Field of Classification Search ........... 606/205–211
See application file for complete search history.

(56) References Cited

U.S. PATENT DOCUMENTS

| 390,561 | A | | 10/1888 | Brown | |
|---|---|---|---|---|---|
| 848,126 | A | * | 3/1907 | Roosevelt | 606/157 |
| 2,333,740 | A | | 5/1943 | Rasmussen | |
| 3,916,910 | A | * | 11/1975 | Seeling et al. | 606/210 |
| 3,980,086 | A | | 9/1976 | Kletschka et al. | |
| 5,147,356 | A | | 9/1992 | Bhatta | |
| 5,336,221 | A | * | 8/1994 | Anderson | 606/27 |
| 5,697,889 | A | * | 12/1997 | Slotman et al. | 600/204 |
| 5,727,569 | A | | 3/1998 | Benetti et al. | |
| 5,891,017 | A | | 4/1999 | Swindle et al. | |
| 6,185,356 | B1 | | 2/2001 | Parker et al. | |
| 6,428,180 | B1 | | 8/2002 | Karram et al. | |
| 6,582,451 | B1 | * | 6/2003 | Marucci et al. | 606/207 |

(Continued)

FOREIGN PATENT DOCUMENTS

| KR | 2003-0325199 | 9/2003 |
|---|---|---|
| KR | 20-0338068 | 1/2004 |

(Continued)

OTHER PUBLICATIONS

Extended European Search Report for Application No. 09010619.6-2319, dated Jul. 13, 2010, consisting of 6 pages.
Extended European Search Report for European Application No. 09010620.4; Date Mailed: Aug. 31, 2010, 6 pages.

(Continued)

*Primary Examiner* — Sam Yao
*Assistant Examiner* — Nathan J Jenness
(74) *Attorney, Agent, or Firm* — Hamilton, Brook, Smith & Reynolds, P.C.

(57) ABSTRACT

Provided is a surgical instrument which can provide a field of view over a surgical site by sucking blood from a bleeding site during surgery on body tissue of a patient and monitoring a dark and deep surgical site, which an operator cannot see with his or her naked eye, with a small camera. The surgical instrument has substantially the same shape as a pair of scissors and includes a first body, a second body having a shape symmetrical to that of the first body, a hinge to which the first and second bodies cross and are rotatably coupled, and a photographing unit provided in the hinge to photograph a surgical site between front ends of the first and second bodies. The photographing unit may include a camera mounted in the hinge such that lens of the camera can be exposed through the center of the front surface of the hinge and configured to transmit a photographed image data to a monitor.

17 Claims, 11 Drawing Sheets

U.S. PATENT DOCUMENTS

| | | |
|---|---|---|
| 2005/0171408 A1 | 8/2005 | Parker |
| 2006/0183975 A1 | 8/2006 | Saadat et al. |
| 2007/0287889 A1 | 12/2007 | Mohr |
| 2008/0097519 A1* | 4/2008 | Calderon et al. ............. 606/205 |
| 2010/0274097 A1 | 10/2010 | Cho et al. |
| 2011/0063428 A1* | 3/2011 | Sonnenschein et al. ........ 348/76 |

FOREIGN PATENT DOCUMENTS

| | | |
|---|---|---|
| KR | 100592944 B1 | 6/2006 |
| KR | 100828135 B1 | 4/2008 |
| WO | WO 03/017847 A1 | 3/2003 |
| WO | WO 2009/004610 A2 | 1/2009 |

* cited by examiner

SURGICAL INSTRUMENT

CROSS-REFERENCE TO RELATED APPLICATION

This application claims priority to and the benefit of Korean Patent Application No. 2009-0039091, filed May 6, 2009, the disclosure of which is incorporated herein by reference in its entirety.

BACKGROUND

1. Technical Field

The present invention relates to surgical instruments, and more particularly, to surgical instruments used in surgery for dissecting body tissue of a patient.

2. Discussion of Related Art

During surgery, an operator may dissect a soft tissue of a patient to obtain a desired surgical field. However, due to the anatomical structure of the human body, there will inevitably be dangerous situations in which the operator cannot obtain a visual field over the surgical site and must perform tissue dissection only under the sensation felt by his or her finger tips. When bleeding occurs during this blind tissue dissection, simple manual compression hemostasis is necessary to attempt to control the bleeding. However, if the bleeding is not controlled by this maneuver, it may cause a dangerous situation for the patient. Even when the bleeding is controlled through the simple manual compression, there is still a high possibility of rebleeding when an operator resumes dissection in the same tissue plane and thus it is difficult for the operator to proceed with further tissue dissection. In the worst case, due to the poor visual field, other important internal organs unrelated to the purpose of the surgery may be damaged. As a result, surgery-related morbidity or mortality rates could be increased.

SUMMARY

Example embodiments of the present invention are directed to provide surgical instruments which allow an operator to obtain a field of view over a surgical site by monitoring a dark and deep surgical site which an operator cannot reach with his or her naked eye, with a small camera during surgery on body tissue of a patient.

Example embodiments of the present invention are also directed to provide surgical instruments which provide a field of view over a surgical site by sucking blood bleeding from a dark and deep surgical site and illuminating the surgical site during surgery on body tissue of a patient, thus allowing an operator to safely and rapidly perform the surgery.

Additional aspects of example embodiments of the invention will be set forth in the description which follows, and in part will be apparent from the description, or may be learned by practice of the invention.

In example embodiments, a surgical instrument includes: a first body; a second body having a shape symmetrical to that of the first body; a hinge to which the first and second bodies cross and are rotatably coupled; and a photographing unit provided in the hinge to photograph a surgical site between front ends of the first and second bodies.

The hinge may include: a hinge body located at a position at which the first and second bodies cross each other; and hinge shafts protruding from upper and lower surfaces of the hinge body and inserted into hinge holes of the first and second bodies to be hinge-coupled thereto, respectively.

The photographing unit may include a camera mounted in the hinge body such that a lens of the camera is exposed through the center of a front surface of the hinge body, and configured to transmit photographed image data to a monitor.

The camera may be arranged to be focused on the center between the opened front ends of the first and second bodies.

The surgical instrument of the present invention may further include an illuminator configured to illuminate the front of the photographing unit.

The illuminator may include optical fibers mounted in the hinge and configured to guide light generated from a light source to be irradiated to the front of the photographing unit.

Front ends of the optical fibers may be exposed from a front surface of the hinge and arranged substantially vertically or horizontally symmetrically with respect to the photographing unit.

The illuminator may include light bulbs or LED lamps disposed on a front surface of the hinge and arranged substantially vertically or horizontally symmetrically with respect to the photographing unit so as to illuminate the front of the photographing unit.

The surgical instrument may further include a camera guide configured to guide the camera to be constantly focused on the center between the opened front ends of the first and second bodies when the first and second bodies rotate about the hinge.

The camera guide may include: a guide rod formed to extend to the rear of the hinge body; a pinion rotatably coupled to the rear end of the guide rod; and a pair of racks provided in the first and second bodies to be engaged with the pinion, respectively, and configured to rotate the pinion during rotation of the first and second bodies and allow the guide rod to be constantly located in the center of the first and second bodies.

The surgical instrument may further include a suction unit configured to suck blood from a bleeding site of a patient during surgery through at least one hole formed at the front end of the first or second body and a fluid supply unit configured to supply fluid through the hole. Here, the hole may be formed on a front surface of the front end or on an inner surface of the first or second body.

A tube may be mounted in the first or second body to be connected to the hole, and the tube may be connected to the suction unit and the fluid supply unit.

A switching valve configured to selectively switch between the blood suction by the suction unit and the fluid supply by the fluid supply unit may be formed in a region in which the suction unit and the fluid supply unit are connected to the tube.

A tube insertion hole may be formed lengthwise in the first or second body such that the tube can be inserted and mounted in the tube insertion hole.

The front ends of the first and second bodies may be bent upward or downward.

Handles may be formed on the rear ends of the first and second bodies such that a user's fingers can be inserted into the handles to hold the surgical instrument.

Each of the first and second bodies may include a hinge receiver configured to receive the hinge body in a region in which the first and second bodies cross and are rotatably coupled to each other such that the first and second bodies do not interfere with the hinge body during rotation.

In other example embodiments, a surgical instrument includes: a first body including at least one hole formed at a front end thereof, a second body having a shape symmetrical to that of the first body and including at least one hole formed at a front end thereof; a hinge to which the first and second bodies cross and are rotatably coupled; a camera mounted in the hinge to photograph a surgical site between the front ends of the first and second bodies; an optical fiber mounted in the hinge and configured to guide light generated from a light source to be irradiated to the front of the camera; a camera guide configured to guide the camera to be constantly focused on the center between the opened front ends of the first and second bodies when the first and second bodies rotate about the hinge; a suction unit configured to suck blood from a bleeding site of a patient during surgery through the hole of the first or second body; and a fluid supply unit configured to supply fluid through the hole of the first or second body.

BRIEF DESCRIPTION OF THE DRAWINGS

The above and other objects, features and advantages of example embodiments of the present invention will become more apparent to those of ordinary skill in the art by describing in detail example embodiments thereof with reference to the attached drawings, in which.

DETAILED DESCRIPTION OF EXAMPLE EMBODIMENTS

Hereinafter, example embodiments of the present invention will be described in detail. However, the present invention is not limited to the embodiments disclosed below, but can be implemented in various forms. The following embodiments are described in order to enable those of ordinary skill in the art to embody and practice the present invention.

Advantages and features of the present invention and methods of accomplishing the same may be understood more readily by reference to the following detailed description of example embodiments and the accompanying drawings. The present invention may, however, be embodied in many different forms and should not be construed as being limited to the example embodiments set forth herein. Rather, these example embodiments are provided so that this disclosure will be thorough and complete and will fully convey the concept of the present invention to those skilled in the art, and the present invention will only be defined by the appended claims. Like reference numerals refer to like elements throughout the specification.

Hereinafter, a surgical instrument in accordance with an example embodiment of the present invention will be described in detail with reference to the accompanying drawings. In the following description, detailed description of well-known functions or constructions that would obscure the invention in unnecessary detail will be omitted.

The term "dissection" used throughout the specification means an action of opening the space between laminated tissues or the space between heterogeneous tissues. Although the example embodiment illustrates a surgical instrument in the form of a body tissue dissector that enters the space between the laminated tissues or the space between heterogeneous tissues and opens the space, the present invention is not limited thereto and may be applied to various types of surgical instruments having shapes other than the dissector.

Figure 1:
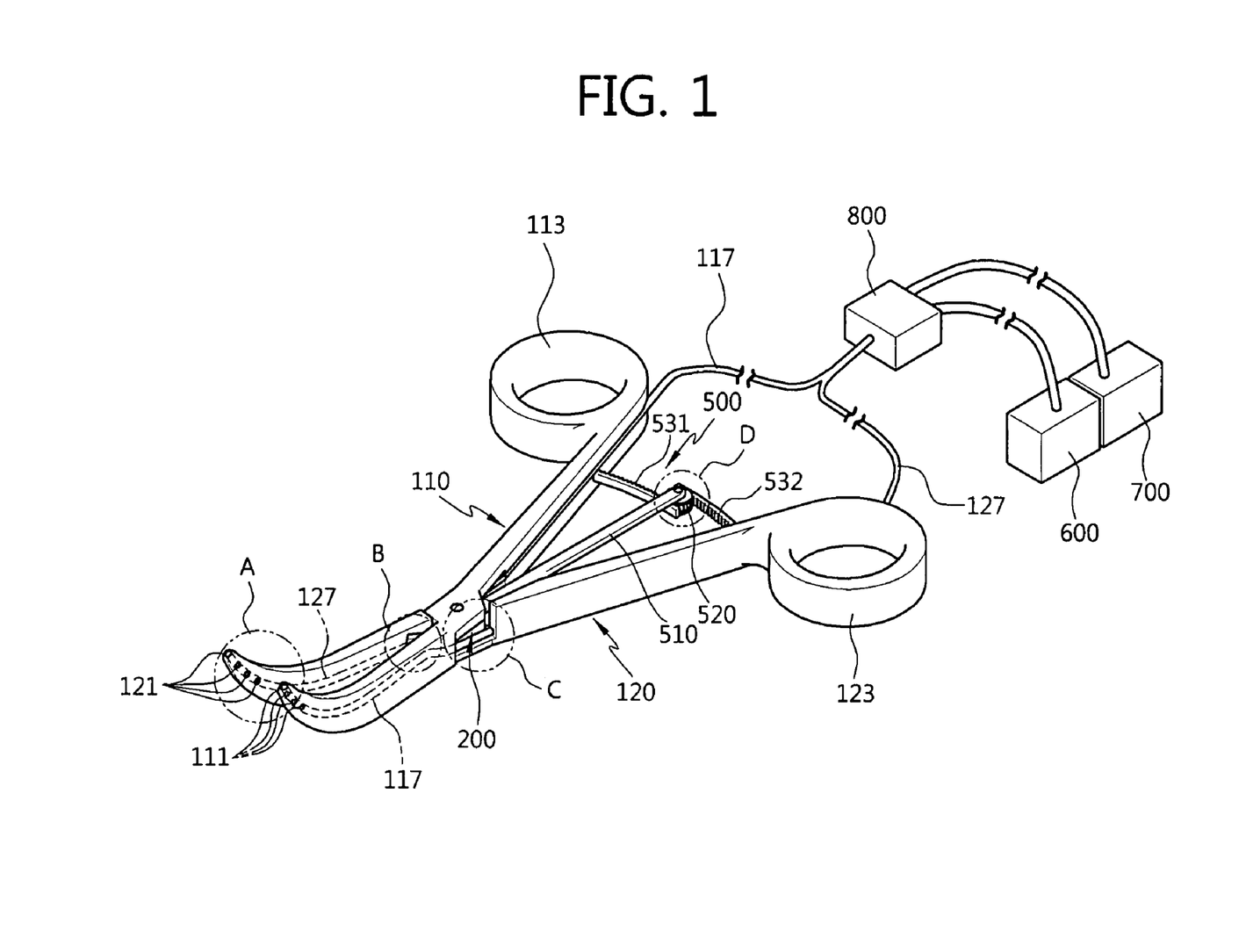
FIG. 1 is a perspective view schematically showing a surgical instrument in accordance with an example embodiment of the present invention.
Figure 2:
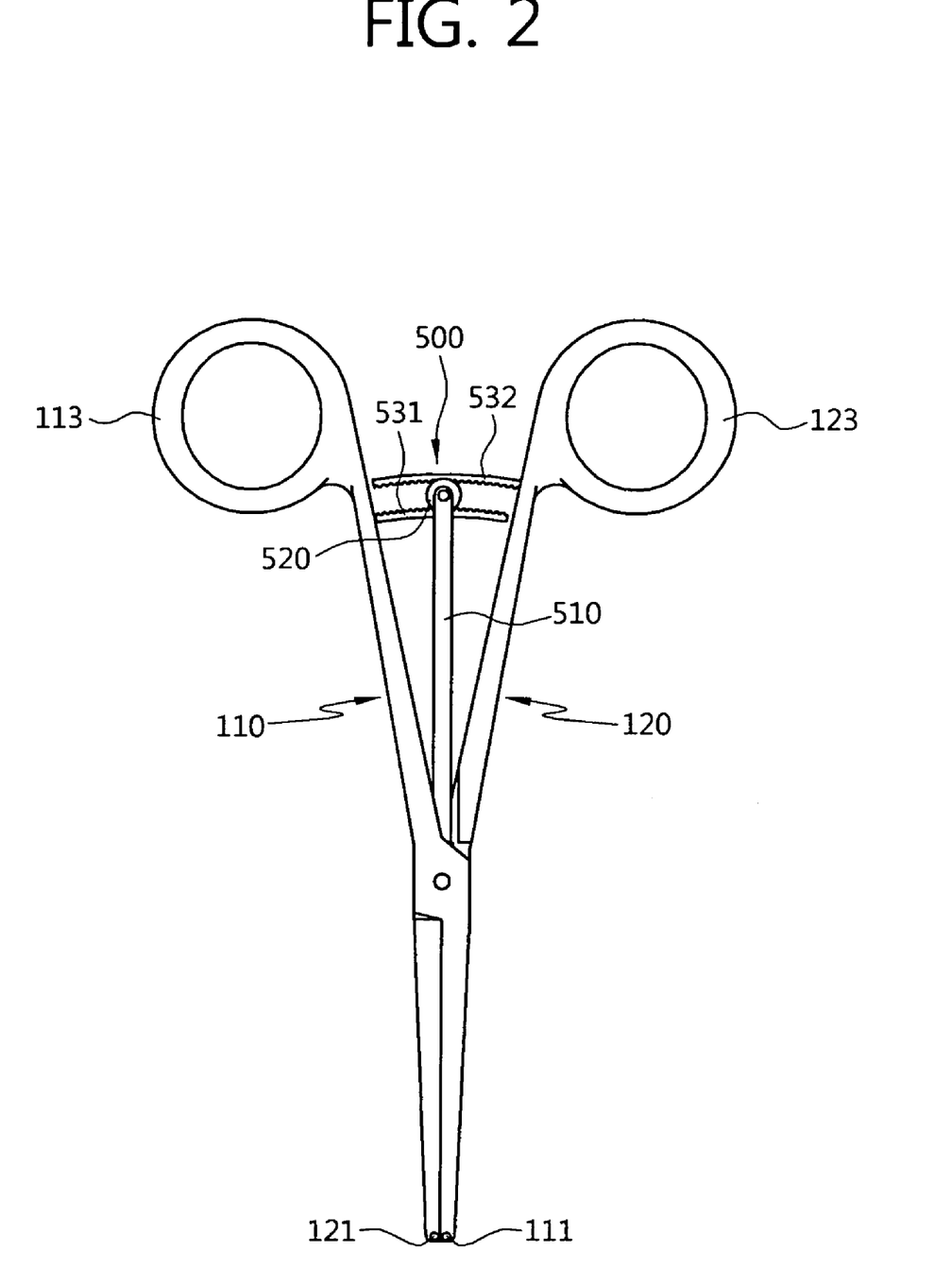
FIG. 2 is a plan view showing a state in which front ends of the surgical instrument in accordance with an example embodiment of the present invention are closed.
Figure 3:
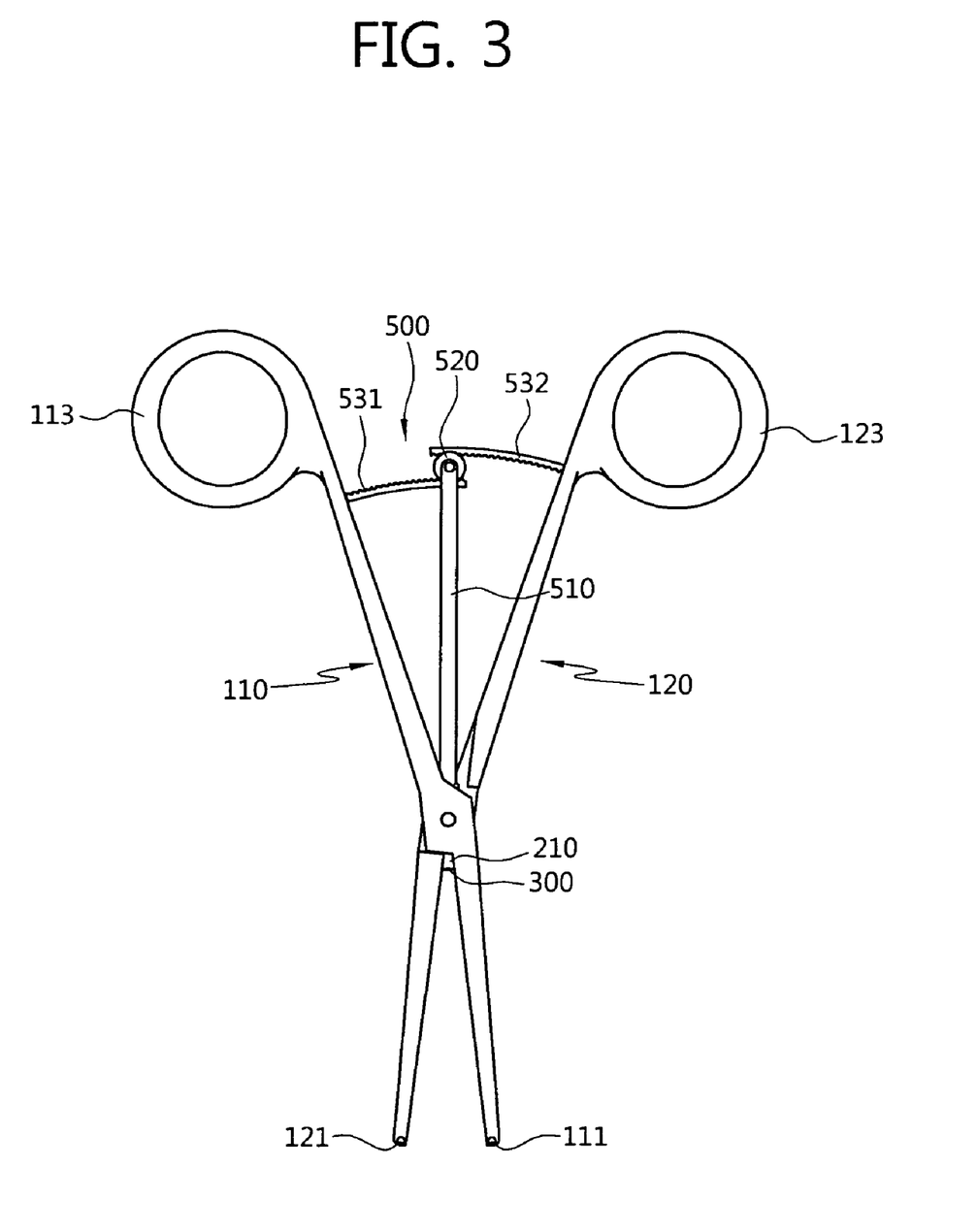
FIG. 3 is a plan view showing a state in which front ends of the surgical instrument in accordance with an example embodiment of the present invention are opened.
Figure 4:
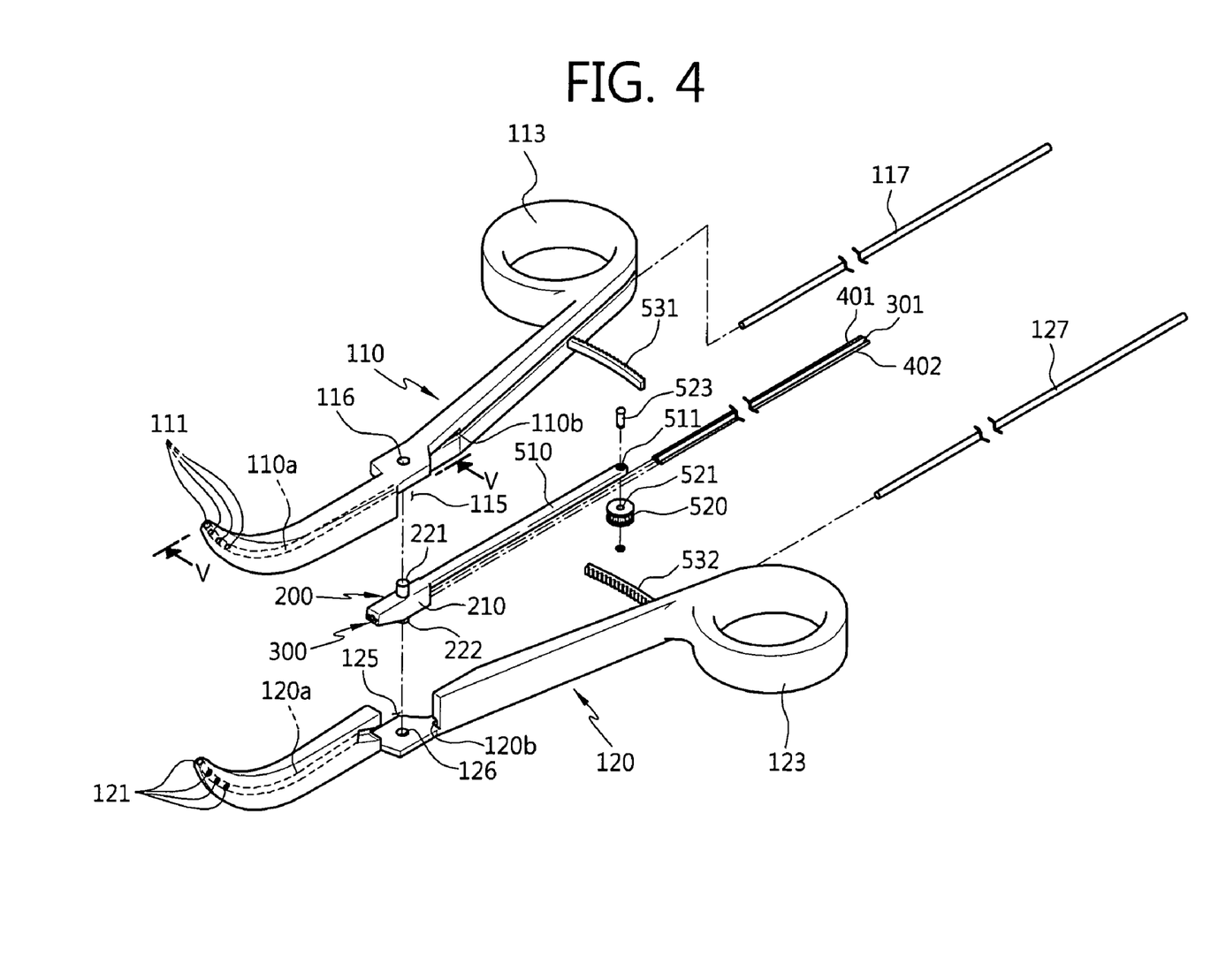
FIG. 4 is an exploded perspective view of the surgical instrument of FIG. 1.
Figure 5:
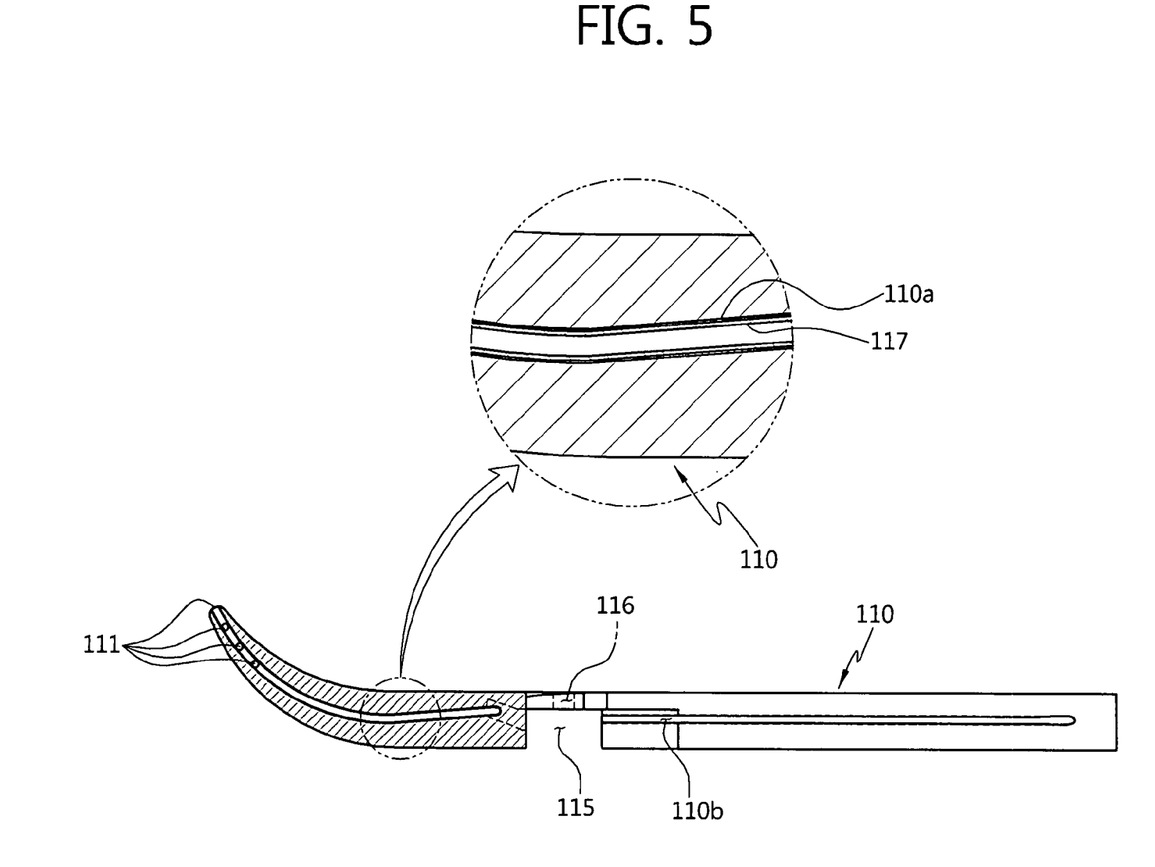
FIG. 5 is a cross-sectional view taken along line V-V of a first body of FIG. 4.
Figure 6:
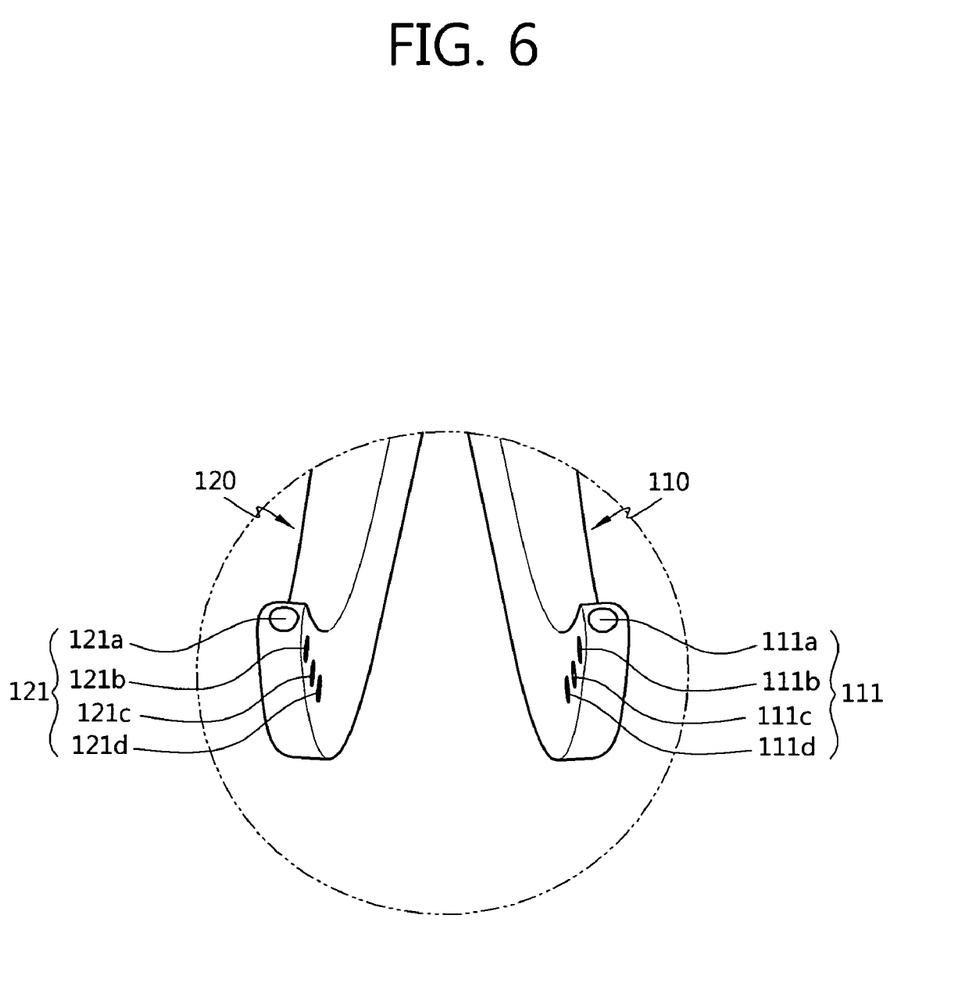
FIG. 6 is an enlarged perspective view of portion A of FIG. 1.
Figure 7:
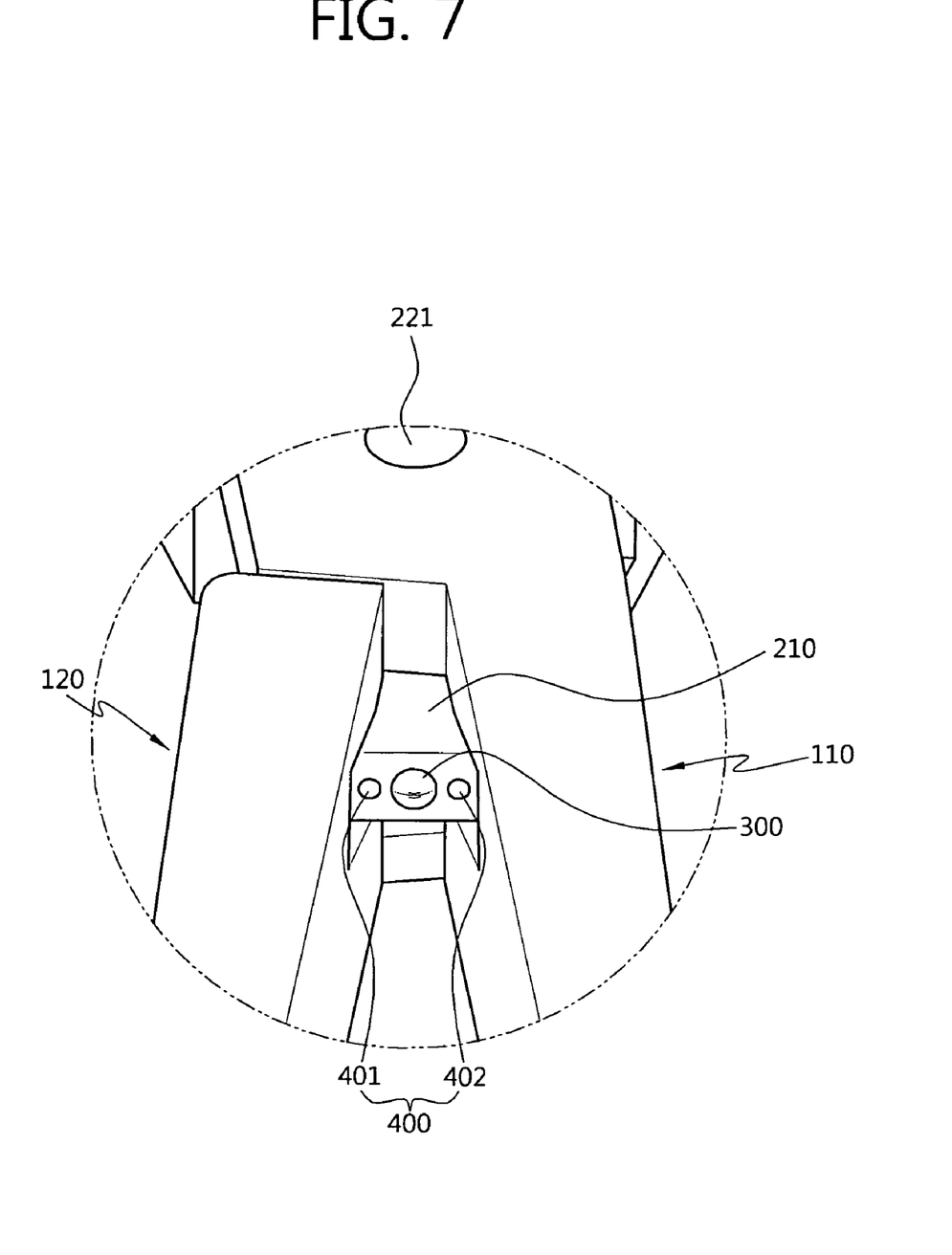
FIG. 7 is an enlarged perspective view of portion B of FIG. 1.
Figure 8:
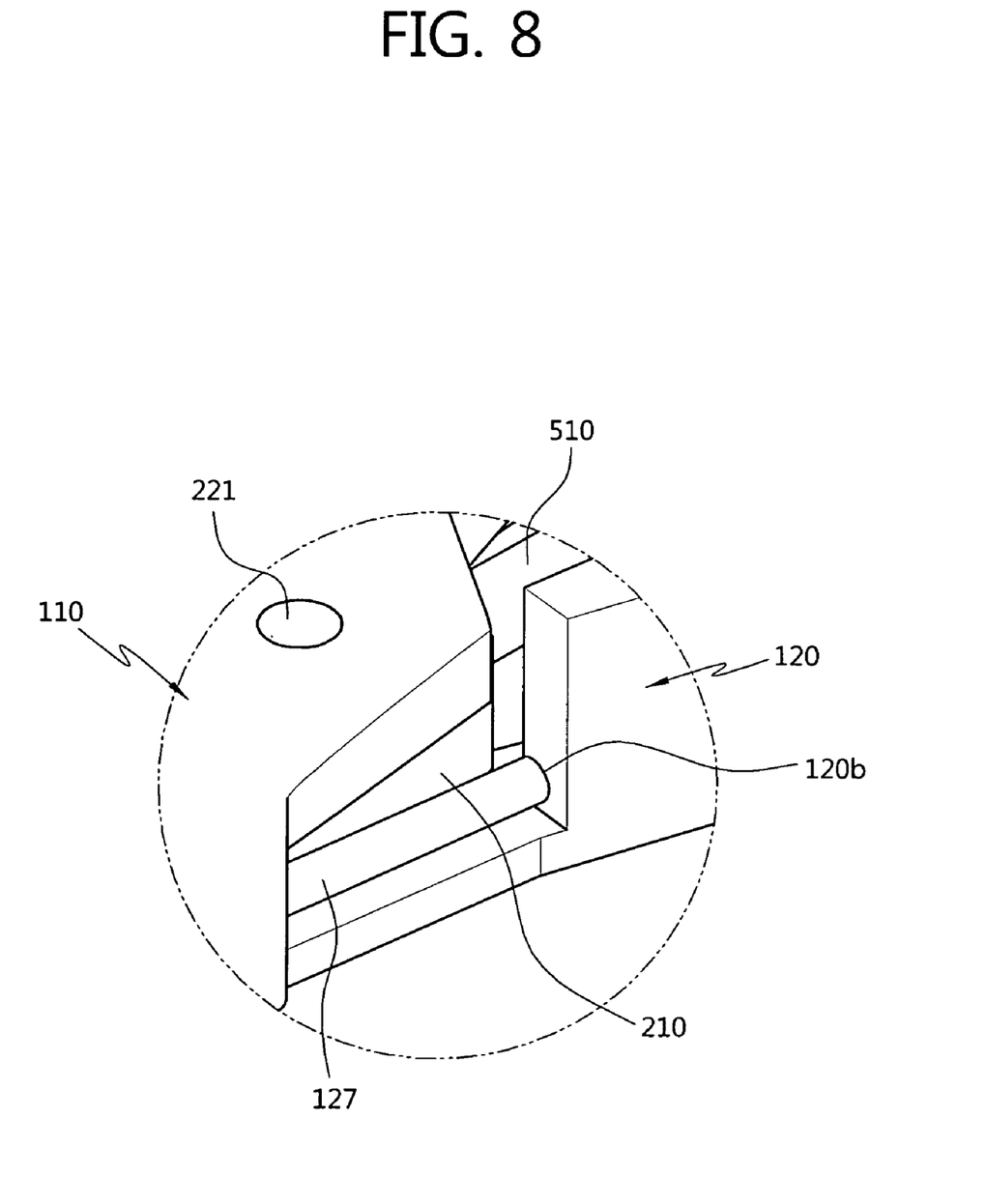
FIG. 8 is an enlarged perspective view of portion C of FIG. 1.
Figure 9:
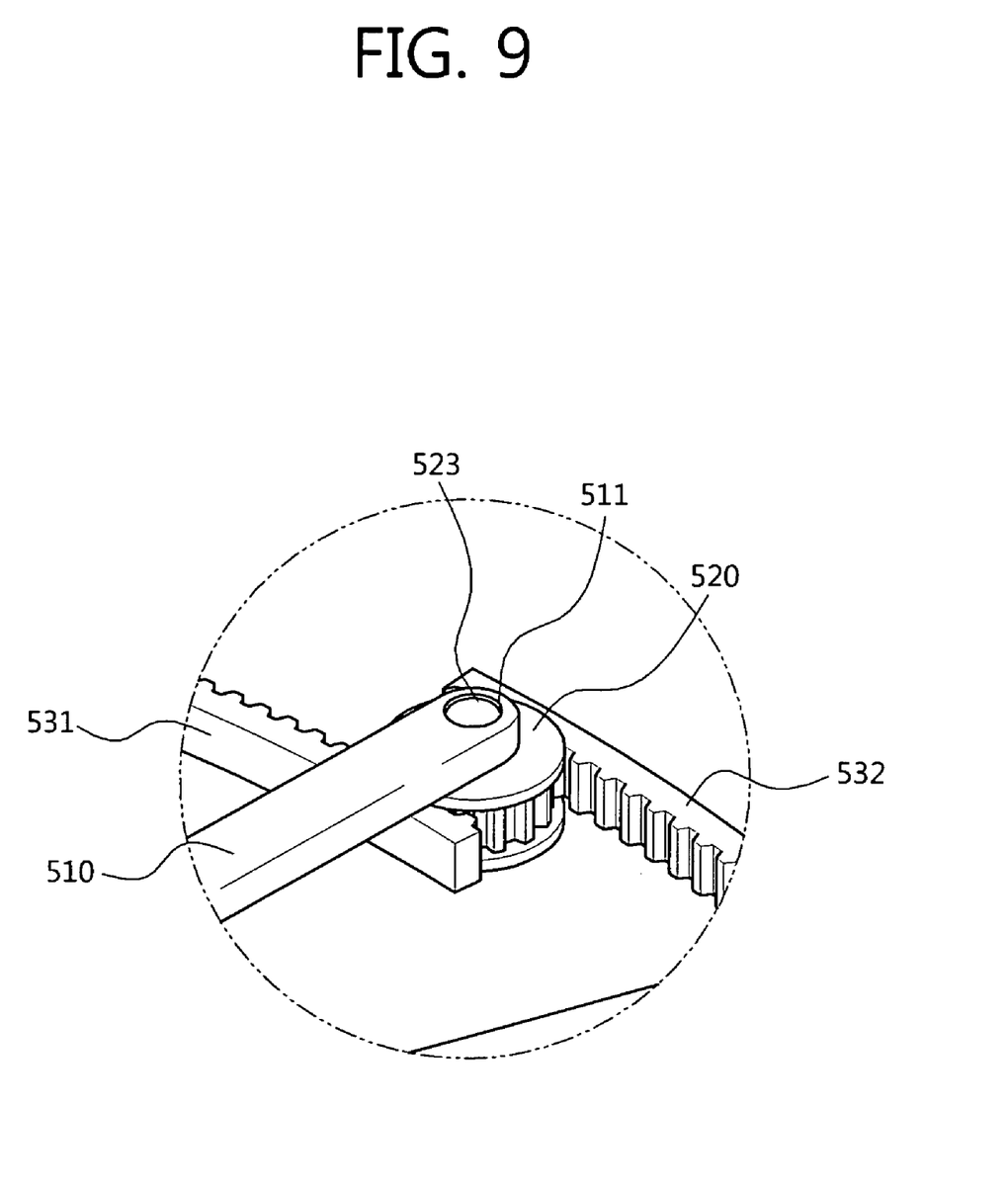
FIG. 9 is an enlarged perspective view of portion D of FIG. 1.
Figure 10:
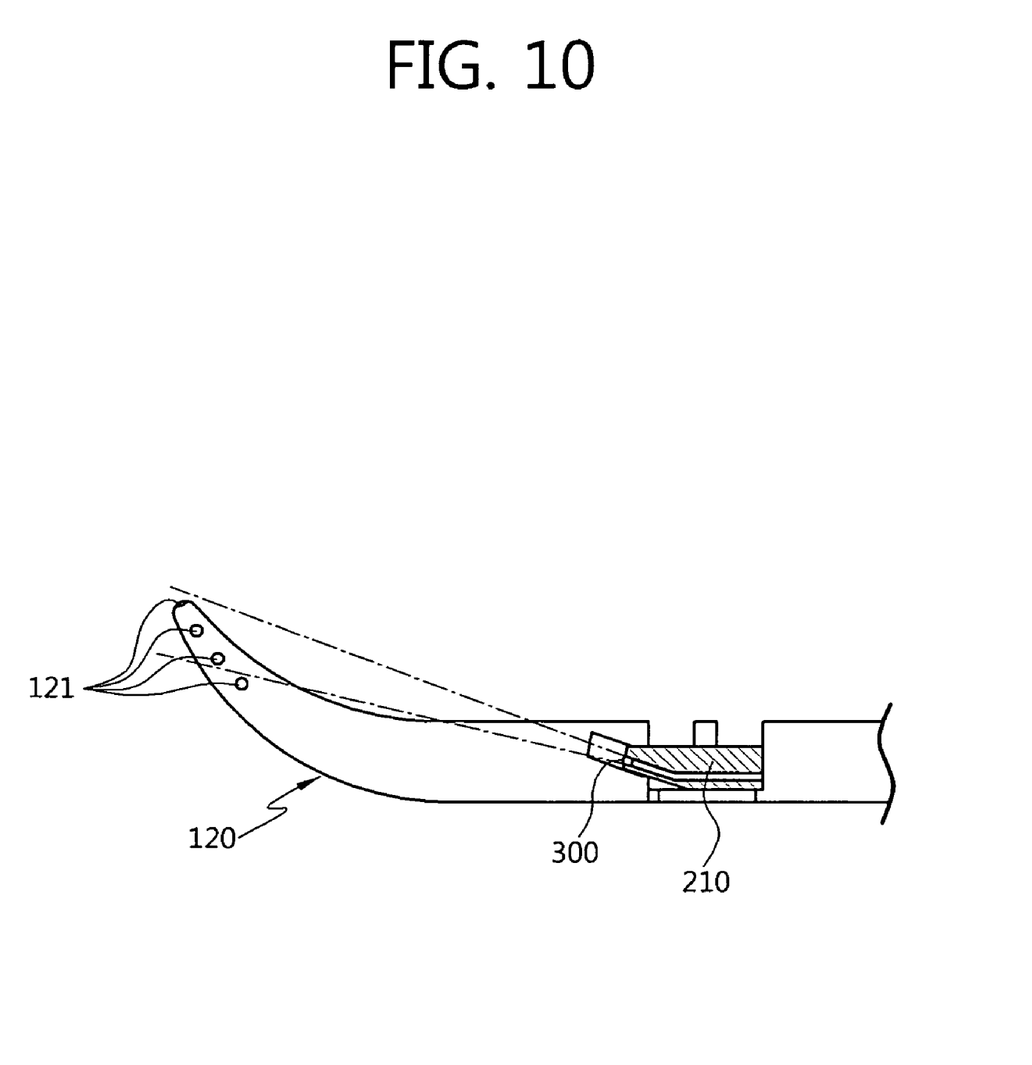
FIG. 10 is an exemplary diagram showing a focus position of a camera mounted in the surgical instrument in accordance with an example embodiment of the present invention.

FIG. 1 is a perspective view schematically showing a surgical instrument in accordance with an example embodiment of the present invention, FIGS. 2 and 3 are plan views showing states where front ends of the surgical instrument in accordance with an example embodiment of the present invention are closed and opened, respectively, FIG. 4 is an exploded perspective view of the surgical instrument of FIG. 1, FIG. 5 is a cross-sectional view taken along line V-V of a first body of FIG. 4, FIGS. 6 to 9 are enlarged perspective views of portions A to D of FIG. 1, and FIG. 10 is an exemplary diagram showing a focus position of a camera mounted in the surgical instrument in accordance with an example embodiment of the present invention.

As shown in FIGS. 1 to 10, the surgical instrument in accordance with an example embodiment of the present invention may include a first body 110, a second body 120, a hinge 200, a photographing unit 300, an illuminator 400, a camera guide 500, a suction unit 600, and a fluid supply unit 700.

The surgical instrument of an example embodiment of the present invention may be configured as a tissue dissector having substantially the same shape as a pair of scissors.

The first and second bodies 110 and 120 correspond to both bodies of the surgical instrument having substantially the same shape as a pair of scissors and are preferably symmetrical with respect to each other.

The first and second bodies 110 and 120 cross each other in substantially the center thereof and are coupled to each other by the hinge 200, which will be described later. In this case, the first and second bodies 110 and 120 may include hinge holes 116 and 126, into which a pair of hinge shafts 221 and 222 protruding from upper and lower surfaces of a hinge body 210, which will be described later, are inserted, each of the hinge holes 116 and 126 being formed in a region where the first and second bodies 110 and 120 are rotatably coupled to each other.

Each of the first and second bodies 110 and 120 may include at least one hole 111 or 121 provided at a front end thereof so as to suck blood from a bleeding site or foreign materials or to discharge fluid (water or liquid medicine) for cleansing or disinfecting the bleeding site during tissue dissection. For example, although the example embodiment illustrates the holes 111 and 121 having a configuration in which each of the holes 111a and 121a is formed on each end of the front surfaces of the first and second bodies 110 and 120 and two or three holes 111b, 111c, and 111d and 121b, 121c, and 121d are formed on each of the inner surfaces thereof, the present invention is not limited thereto, and the holes 111 and 121 may have various numbers and shapes. Moreover, although the hole 111 or 121 may be formed at one of the front ends of the first and second bodies 110 and 120, it is more preferable that the holes 111 and 121 be formed at both of the front ends of the first and second bodies 110 and 120 in the example embodiment. These holes 111 and 121 may be configured to communicate with tube insertion holes 110a and 120a, which will be described later, and also connected to front ends of tubes 117 and 127, which will also be described later. Rear ends of the tubes 117 and 127 may be connected to the suction unit 600 and the fluid supply unit 700 through a switching valve 800, which will be described later.

The tube insertion holes 110a and 120a may be formed lengthwise in the first and second bodies 110 and 120 such that the tubes 117 and 127 can be inserted and mounted in the tube insertion holes 110a and 120a. The example embodiment illustrates a configuration in which the tube insertion holes 110a and 120a penetrate the centers of the first and second bodies 110 and 120 from the front ends of the first and second bodies 110 and 120 to substantially the centers thereof, where the hinge 200 is located, such that the tubes 117 and 127 can be inserted and completely mounted in the tube insertion holes 110a and 120a. Further, tube fixing grooves 110b and 120b may be formed in the form of semispherical grooves on inner surfaces of the first and second bodies 110 and 120 from the centers of the first and second bodies 110 and 120 to the rear ends thereof such that outer diameters of the tubes 117 and 127 can be inserted and fixed into the tube fixing grooves 110 and 120b. However, the tube insertion holes 110a and 120a may be configured to penetrate the entire centers of the first and second bodies 110 and 120 lengthwise such that the tubes 117 and 127 can be inserted from the front ends of the first and second bodies 110 and 120 to the rear ends thereof and completely mounted in the tube insertion holes 110a and 120a.

The tube insertion holes 110a and 120a may have a diameter greater than that of the holes 111 and 120 to prevent the blood or foreign materials sucked into the tube insertion holes 110a and 120a through the holes 111 and 121 formed at the front ends of the first and second bodies 110 and 120 from being caught. Moreover, the diameters of the tube insertion holes 110a and 120a may increase from the front ends of the first and second bodies 110 and 120 toward the rears thereof.

The front ends of the first and second bodies 110 and 120 may be bent upward or downward so as to easily open the space between tissues. Moreover, handles 113 and 123 may be formed in the form of rings at the rear ends of the first and second bodies 110 and 120 such that an operator's fingers can be inserted therethrough to hold the surgical instrument.

The first and second bodies 110 and 120 may include hinge receivers 115 and 125 having a space capable of receiving the hinge body 210 and formed in a region where the first and second bodies 110 and 120 are rotatably coupled to each other such that the first and second bodies 110 and 120 do not interfere with the hinge body 210 during rotation about the hinge 200.

The hinge 200 may be coupled between the first and second bodies 110 and 120 such that the first and second bodies 110 and 120 can be rotatably coupled to each other about the hinge 200. For example, the first body 110 may be located on the top of the hinge 200 and the second body 120 may be located at the bottom thereof such that the first and second bodies 110 and 120 can be rotatably coupled to the top and bottom of the hinge 200.

The hinge 200 may include the hinge body 210 and the pair of hinge shafts 221 and 222. The hinge body 210 may be located in a position at which the first and second bodies 110 and 120 cross each other, and the pair of hinge shafts 221 and 222 may protrude from the upper and lower surfaces of the hinge body 210 and be inserted into the hinge holes 116 and 126 of the first and second bodies 110 and 120 to be hinge-coupled thereto. In this case, the hinge body 210 may have a shape capable of being received in the hinge receivers 115 and 125 of the first and second bodies 110 and 120 such that the hinge body 210 does not interfere with the first and second bodies 110 and 120 during rotation. For example, although the example embodiment illustrates a configuration in which the hinge body 210 has a substantially rectangular parallelepiped shape having a size smaller than that of the hinge receivers 115 and 125 of the first and second bodies 110 and 120, the present invention is not limited thereto, and the hinge body 210 may be formed into various shapes such as a circular plate shape having a small radius so as to be received in the hinge receivers 115 and 125.

Moreover, a camera 300, which will be described later, may be mounted in the hinge body 210 such that a lens of the camera 300 can be exposed through the center of the front surface, and a cable insertion hole (not shown) may be formed to penetrate the center of the hinge body 210 lengthwise such that a camera connection cable 301, which will be described later, can be inserted and mounted in the cable insertion hole. Furthermore, optical fiber insertion holes (not shown) may be formed to penetrate both sides of the camera connection cable 301 lengthwise in the hinge body 210 such that optical fibers 401 and 402, which will be described later, can be inserted and mounted in the optical fiber insertion holes.

The photographing unit 300 may be provided in the hinge 200 to photograph the central portion of the dissected tissue between the front ends of the first and second bodies 110 and 120 during tissue dissection in which the surgical instrument enters the space between body tissues and opens the space. For example, the photographing unit 300 may include a small CCD camera (hereinafter, designated by reference numeral 300) mounted therein such that the lens of the camera can be exposed through the center of the front surface of the hinge body 210. In this case, the camera 300 may be arranged to be focused on the center between the opened front ends of the first and second bodies 110 and 120. Moreover, in order to transmit image data photographed by the camera 300 to a monitor (not shown), the camera connection cable 301 may be inserted into the cable insertion hole of the hinge body 210. In this case, the front end of the camera connection cable 301 may be coupled to the camera 300 and the rear end thereof may be coupled to the monitor.

When the operator inserts the surgical instrument deeper into the tissue, the depth of the dissected tissue is increased, and thus the surgical site becomes darker. Therefore, the illuminator 400 is provided in the hinge 200 to illuminate the front of the camera 300 so as to obtain a surgical field of view.

The illuminator 400 may be inserted and mounted in the hinge body 210 and include the optical fibers 401 and 402 configured to guide light generated from a light source (not shown) to be irradiated to the front of the camera 300, specifically, on the center of the dissected tissue between the front ends of the first and second bodies 110 and 120. Here, the light source may include various types of light generating devices capable of providing light to the optical fibers 401 and 402 and may be a light emitting diode (LED). The optical fibers 401 and 402 may be inserted into the optical fiber insertion holes formed to penetrate both sides of the camera connection cable 301 lengthwise in the hinge body 210. Front ends of the optical fibers 401 and 402 may be exposed from the front surface of the hinge body 210 and rear ends may be connected to the light source.

Although the example embodiment illustrates a configuration in which the illuminator 400 includes the optical fibers 401 and 402, the present invention is not limited thereto, and the illuminator 400 may include light bulbs or LED lamps disposed on the front surface of the hinge body 210 and arranged vertically or horizontally symmetrically with respect to the camera 300 to illuminate the front of the camera 300.

The camera guide 500 may be configured to guide the camera 300 mounted in the hinge body 210 to be constantly focused on the center between the opened front ends of the first and second bodies 110 and 120 when the first and second bodies 110 and 120 rotate about the hinge 200.

The camera guide 500 may include a guide rod 510, a pinion 520, and a pair of racks 531 and 532.

The guide rod 510 may be formed in a rod shape extending to the rear of the hinge body 210. Although not shown in the figures, a through hole (not shown) may be formed in the guide rod 510 such that the rear ends of the camera connection cable 301 and the optical fibers 401 and 402 mounted in the hinge body 210 can be inserted into the through hole and extend along the guide rod 510. A shaft hole 511 is formed at the rear end of the guide rod 510 such that a pinion shaft 523, which will be described later, vertically penetrates. Here, the pinion shaft 523 is vertically located in parallel to the hinge shafts 221 and 222 of the hinge body 210.

The pinion 520 may be rotatably coupled to the rear end of the guide rod 510. In this case, a shaft hole 521, through which the pinion shaft 523 is vertically inserted, may be formed in the center of the pinion 520.

The pair of racks 531 and 532 may be provided in the first and second bodies 110 and 120, respectively, to be engaged with the pinion 520. The pair of racks 531 and 532 may rotate the pinion 520 disposed between the pair of racks 531 and 532 during rotation of the first and second bodies 110 and 120 and allow the guide rod 510 to be constantly located in the center of the first and second bodies 110 and 120. In further detail, the first rack 531 may be formed at the rear end of the first body 110 to protrude toward the second body 120 such that it can be engaged with the inner surface of the pinion 520, and the second rack 532 may be formed at the rear end of the second body 120 to protrude toward the first body 110 such that it can be engaged with the outer surface of the pinion 520. Teeth may be formed on the outer surface of the first rack 531 to be engaged with the inner surface of the pinion 520, and teeth may be formed on the inner surface of the second rack 532 which faces the outer surface of the first rack 531 to be engaged with the outer surface of the pinion 520. That is, the first and second racks 531 and 532 are disposed to face each other with the pinion 520 interposed therebetween and may have an arc shape with respect to the rotational center of the hinge 200. In this case, when the front ends of the surgical instrument are closed (see FIG. 2), the pinion 520 may be located in the center of the first and second racks 531 and 532. Whereas, when the front ends of the surgical instrument are opened maximally (see FIG. 3), the pinion 520 may be located at the ends of the first and second racks 531 and 532. Thus, the guide rod 510 can be constantly located in the center of the first and second bodies 110 and 120 by the pinion 520 and the pair of racks 531 and 532 during the rotational movement of the surgical instrument in which the front ends are closed and opened. As a result, it is possible to guide the camera 300 mounted in the hinge 200 to be constantly focused on the center of the dissected tissue between the front ends of the first and second bodies 110 and 120.

The suction unit 600 may be connected to the tubes 117 and 127 to suck blood from the bleeding site or foreign materials generated during surgery such as tissue dissection through the holes 111 and 121 formed at the front end of the first or second body 110 or 120. Here, the suction unit 600 may be exemplified as an air suction device that uses air.

The fluid supply unit 700 may be connected to the tubes 117 and 127 to supply fluid such as water, antiseptic liquid, or liquid medicine so as to clean the bleeding site or inject the liquid medicine into the surgical site during surgery such as tissue dissection through the holes 111 and 121 formed at the front end of the first or second body 110 or 120.

The switching valve 800 is provided in the center where the suction unit 600 and the fluid supply unit 700 are connected to the tubes 117 and 127 so as to selectively switch between the suction of the blood or foreign materials by the suction unit 600 and the fluid supply by the fluid supply unit 700. Here, since the suction unit 600, the fluid supply unit 700, and the switching valve 800 are well-known elements, detailed descriptions thereof will be omitted.

Next, the operation of the surgical instrument in accordance with an example embodiment of the present invention will be described in detail with reference to FIG. 11.

Figure 11:
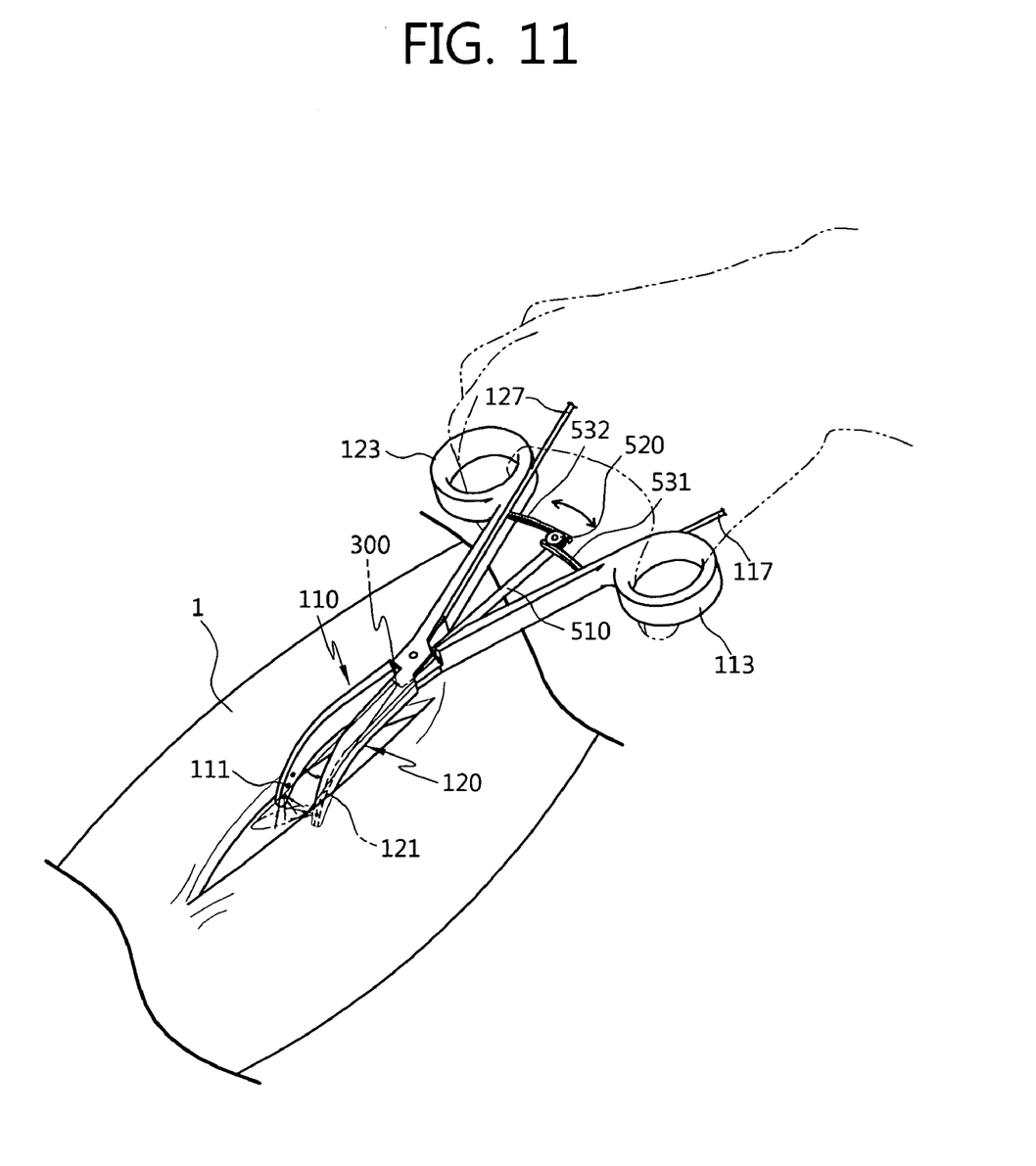
FIG. 11 is an exemplary diagram illustrating use of the surgical instrument in accordance with an example embodiment of the present invention.

FIG. 11 is an exemplary diagram illustrating use of the surgical instrument in accordance with an example embodiment of the present invention.

As shown in FIG. 11, an operator inserts his or her fingers into the handles 113 and 123 of the surgical instrument to hold the surgical instrument and inserts the surgical instrument into a patient's body. At this time, the operator performs tissue dissection, in which the space between tissues is opened while both front ends of the surgical instrument are facing downward, and enters a desired surgical site. Here, bleeding occurs in the dissected tissue during the tissue dissection. Therefore, when the switching valve 800 is switched such that the tubes 117 and 127 mounted in the first and second bodies 110 and 120 are connected to the suction unit 600, the blood from the bleeding site and foreign materials generated during surgery are sucked through the holes 111 and 121 provided at the front ends coupled to the tubes 117 and 127, thereby providing a surgical field of view. Moreover, when the switching valve 800 is switched such that the tubes 117 and 127 are connected to the fluid supply unit 700, fluids such as water, antiseptic liquid, and liquid medicine are discharged through the holes 111 and 121 connected to the tubes 117 and 127, thereby cleansing the bleeding site or injecting the liquid medicine into the surgical site.

When the operator inserts the surgical instrument deeper into the tissue to a desired surgical site, the depth of the dissected tissue is increased, and thus the operator cannot see the surgical site with his or her naked eye. As a result, it is difficult for the operator to obtain a better surgical field of view. At this time, the small camera 300 mounted in the hinge 200 of the surgical instrument photographs the surgical site during surgery such as tissue dissection and outputs the photographed image data to the monitor (not shown). Thus, the operator can obtain the field of view over the surgical site, which the operator cannot see with his or her naked eye, through the monitor connected to the camera 300. As a result, it is possible to prevent major blood vessels or other important internal organs from being damaged during surgery such as tissue dissection, thus reducing the surgical risk. At this time, the guide rod 510 is constantly located in the center of the first and second bodies 110 and 120 by the pinion 520 and the pair of racks 531 and 532 during the rotational movement of the surgical instrument in which the front ends are closed and opened. As a result, the camera 300 mounted in the hinge 200 connected to the guide rod 510 is constantly focused the center of the dissected tissue between the front ends of the first and second bodies 110 and 120.

Moreover, it is possible to illuminate the surgical site between the front ends of the first and second bodies 110 and 120 by guiding light generated from a light source to be irradiated on the surgical site between the front ends of the first and second bodies 110 and 120 using the optical fibers 401 and 402 mounted in the hinge 200, thus obtaining the surgical field of view.

Furthermore, since the surgical instrument according to an example embodiment of the present invention has substantially the same shape as a pair of scissors, it is easy for the operator to master the use of the surgical instrument.

As described above, according to a surgical instrument according to an example embodiment of the present invention, it is possible to allow an operator to obtain a field of view over a surgical site by monitoring a dark and deep surgical site, which an operator cannot see with his or her naked eye, with a small camera during surgery on body tissue of a patient. As a result, it is possible to prevent major blood vessels or other important internal organs from being damaged during surgery such as tissue dissection, thus reducing the surgical risk.

Moreover, it is possible to provide a field of view over a surgical site by sucking blood from a bleeding site caused in a dark and deep surgical site, supplying fluid for cleaning the bleeding site, and illuminating the surgical site during surgery on body tissue of a patient, thus allowing the operator to safely and rapidly perform the surgery.

Furthermore, since the surgical instrument according to an example embodiment of the present invention has substantially the same shape as a pair of scissors, it is easy for the operator to master the use of the surgical instrument.

While the example embodiments of the present invention have been described with reference to the accompanying drawings, it will be apparent to those skilled in the art that various modifications and variations can be made in the present invention without departing from the scope of the invention. Thus, it is intended that any future modifications of the embodiments of the present invention will come within the scope of the appended claims and their equivalents.

What is claimed is:

1. A surgical instrument comprising:
   a first body having a front end;
   a second body having a front end;
   a hinge to which the first and second bodies cross and are rotatably coupled to open and close the front ends;
   a photographing unit provided in the hinge, comprising a camera configured to photograph a surgical site between front ends of the first and second bodies and to transmit photographed image data; and
   a camera guide configured to guide the camera to be constantly focused on the center between the opened front ends of the first and second bodies when the first and second bodies rotate about the hinge,
   wherein the second body has a shape symmetrical to that of the first body in a range from the hinge to a rear end;
   wherein the camera guide comprises:
      a guide rod formed to extend to the rear of the hinge;
      a pinion rotatably coupled to the rear end of the guide rod; and
      a pair of racks provided in the first and second bodies to be engaged with the pinion, respectively, and configured to rotate the pinion during rotation of the first and second bodies and allow the guide rod to be constantly located in the center of the first and second bodies.

2. The surgical instrument of claim 1, wherein the hinge comprises:
   a hinge body located at a position at which the first and second bodies cross each other; and
   hinge shafts protruding from upper and lower surfaces of the hinge body and inserted into hinge holes of the first and second bodies to be hinge-coupled thereto, respectively.

3. The surgical instrument of claim 2, wherein the camera is mounted in the hinge body such that a lens of the camera is exposed through the center of a front surface of the hinge body, and configured to transmit the photographed image data to a monitor.

4. The surgical instrument of claim 1, further comprising an illuminator configured to illuminate the front of the photographing unit.

5. The surgical instrument of claim 4, wherein the illuminator comprises optical fibers mounted in the hinge and configured to guide light generated from a light source to the front of the photographing unit.

6. The surgical instrument of claim 5, wherein front ends of the optical fibers are exposed from a front surface of the hinge and arranged vertically or horizontally symmetrical with respect to the photographing unit.

7. The surgical instrument of claim 4, wherein the illuminator comprises light bulbs or LED lamps disposed on a front surface of the hinge and arranged vertically or horizontally symmetrical with respect to the photographing unit so as to illuminate the front of the photographing unit.

8. The surgical instrument of claim 1, further comprising a suction unit configured to suck blood from a bleeding site of a patient during surgery through at least one hole formed at the front end of the first or second body.

9. The surgical instrument of claim 8, further comprising a fluid supply unit configured to supply fluid through the hole.

10. The surgical instrument of claim 8, wherein a tube is mounted in the first or second body to be connected to the hole, and the tube is connected to the suction unit and the fluid supply unit.

11. The surgical instrument of claim 10, wherein a switching valve, configured to selectively switch between the blood suction by the suction unit and the fluid supply by the fluid supply unit, is formed in a region in which the suction unit and the fluid supply unit are connected to the tube.

12. The surgical instrument of claim 10, wherein a tube insertion hole is formed lengthwise in the first or second body such that the tube is inserted and mounted in the tube insertion hole.

13. The surgical instrument of claim 8, wherein the hole is formed on a front surface of the front end or on an inner surface of the first or second body.

14. The surgical instrument of claim 1, wherein the front ends of the first and second bodies are bent upward or downward.

15. The surgical instrument of claim 1, wherein handles are formed on rear ends of the first and second bodies such that a user's fingers can be inserted into the handles to hold the surgical instrument.

16. The surgical instrument of claim 2, wherein each of the first and second bodies comprises a hinge receiver configured to receive the hinge body in a region in which the first and second bodies cross and are rotatably coupled to each other such that the first and second bodies do not interfere with the hinge body during rotation.

17. A surgical instrument comprising:
a first body including at least one hole formed at a front end thereof;
a second body including at least one hole formed at a front end thereof;
a hinge to which the first and second bodies cross and are rotatably coupled to open and close the front ends;
a camera mounted in the hinge to photograph a surgical site between the front ends of the first and second bodies;
an optical fiber mounted in the hinge and configured to guide light generated from a light source to the front of the camera;
a camera guide configured to guide the camera to be constantly focused on the center between the opened front ends of the first and second bodies when the first and second bodies rotate about the hinge;
a suction unit configured to suck blood from a bleeding site of a patient during surgery through the hole of the first or second body; and
a fluid supply unit configured to supply fluid through the hole of the first or second body,
wherein the second body has a shape symmetrical to that of the first body in a range from the hinge to a rear end;
wherein the camera guide comprises:
a guide rod formed to extend to the rear of the hinge;
a pinion rotatably coupled to the rear end of the guide rod; and
a pair of racks provided in the first and second bodies to be engaged with the pinion, respectively, and configured to rotate the pinion during rotation of the first and second bodies and allow the guide rod to be constantly located in the center of the first and second bodies.

* * * * *